(12) United States Patent
Bergmann et al.

(10) Patent No.: US 8,013,123 B2
(45) Date of Patent: Sep. 6, 2011

(54) USE OF PRECURSORS OF ENKEPHALINS AND/OR THEIR FRAGMENTS IN MEDICAL DIAGNOSTICS

(75) Inventors: Andreas Bergmann, Berlin (DE); Andrea Ernst, Hennigsdorf (DE)

(73) Assignee: B.R.A.H.M.S. GmbH, Hennigsdorf (DE)

( * ) Notice: Subject to any disclaimer, the term of this patent is extended or adjusted under 35 U.S.C. 154(b) by 164 days.

(21) Appl. No.: 11/569,023

(22) PCT Filed: May 11, 2005

(86) PCT No.: PCT/EP2005/005090
§ 371 (c)(1), (2), (4) Date: Aug. 23, 2007

(87) PCT Pub. No.: WO2005/114222
PCT Pub. Date: Dec. 1, 2005

(65) Prior Publication Data
US 2008/0261232 A1 Oct. 23, 2008

(30) Foreign Application Priority Data
May 13, 2004 (EP) .................................... 04090191

(51) Int. Cl.
C07K 16/00 (2006.01)
A61K 39/395 (2006.01)
G01N 33/53 (2006.01)

(52) U.S. Cl. ............. 530/387.1; 530/388.23; 424/130.1; 424/139.1

(58) Field of Classification Search .................. None
See application file for complete search history.

(56) References Cited

FOREIGN PATENT DOCUMENTS

| EP | 1104808 A1 | 6/2001 |
| EP | 1284297 A2 | 2/2003 |
| JP | 63111465 | 5/1988 |
| WO | 03035907 | 5/2003 |

OTHER PUBLICATIONS

Masahiro Kobari et al., Neurological research, 1988, vol. 10, No. 2, pp. 120-122.*
Koch et al., "Distribution and Quantitation of Gut Neuropeptides in Normal Intestine and Inflammatory Bowel Diseases", Digestive Diseases and Sciences, vol. 32(4) Apr. 1987, 369-376.
R. Smith et al., "Studies on Circulating Met-Enkephalin and β-Endorphin: Normal Subjects and Patients with Renal and Adrenal Disease", Clinical Endocrinology (1981) vol. 15, 291-300.
Stachura et al., "Concentration of enkephalins in cerebrospinal fluid of patients after severe head injury", Neuropeptides 1997, vol. 31(1), 78-81.
Roger Smith et al., "Effect of Liver and Renal Dysfunction on Circulating Methionine-Enkephalin Immunoreactivity", Neuroscience Letters, 60, 1985, 301-305.
S.J. Augood et al., "Reduction in Enkephalin and Substance P Messenger RNA in the Striatum of Early Grade Huntington's Disease: A Detailed Cellular In Situ Hybridization Study", Neuroscience 1996, vol. 72(4), 1023-1036.
A. Böttger et al., "Proenkephalin Is a Nuclear Protein Responsive to Growth Arrest and Differentiation Signals", The Journal of Cell Biology, vol. 130(6), Sep. 1995, 1251-1262.
Stevel L. Sabol et al., "In Vitro Biosynthesis and Processing of Immunologically Identified Methionine-Enkephalin Precursor Protein", The Journal of Biological Chemistry, vol. 258(4), Feb. 25, 1983 issue, 2697-2704.
Volker Böttger et al., "Comprehensive Epitope Analysis of Monoclonal Anti-proenkephalin Antibodies using Phage Display Libraries and Synthetic Peptides: Revelation of Antibody Fine Specificities Caused by Somatic Mutations in the Variable Region Genes", J. Mol. Biol. 247: 932-946 (1995).
Kraemer et al., "Changes in plasma proenkephalin peptide F and catecholamine levels during graded exercise in men", Pro. Natl. Acad. Sci. USA, vol. 82, Sep. 1985, 6349-6351.
Stark et al., "Peptide repertoire of human cerebrospinal fluid: novel proteolytic fragments of neuroendocrine proteins", Journal of Chromatography B. 754 (2001) 357-367.

* cited by examiner

*Primary Examiner* — Olga N Chernyshev
(74) *Attorney, Agent, or Firm* — Heslin Rothenberg Farley & Mesiti P.C.

(57) ABSTRACT

The invention relates to the diagnosis of disease based on the presence of biochemical components in human or animal body fluids, tissues and/or biomaterials. More specifically the invention relates to the use of precursors of enkephalins and/ or its fragments isolated from body fluids, tissues or other biomaterials as a marker peptide for detection of a number of diseases/disorders including diseases/disorders of the central nervous system, neurodegenerative diseases, Parkinson's disease, Alzheimer's disease, Huntington's disease, ischemia including myocardiac ishcemica, schizophrenia, disease/disorders of the immune system, diseases/conditions of pain, chronic pain, migraine, tension type headache, tumor diseases/cancer including lymphoblastic leukaemia, malignant brain tumors, adenomas, in particular human pituitary adenomas, disorders of the blood brain barrier, multiple sclerosis, inflammation, chronic arthritis, infectious diseases, bacterial and viral infections, in particular infections of Gram-positive bacteria, borna diseases virus infections, peritonitis, intoxication, AIDS, stress, trauma comprising head trauma, infarction, in particular cerebral infarction, heart and cardiovascular diseases including coronary heart disease, bone and skin disorders, malaria chronic/obstructive pulmonary disease and cerebral damage. The invention further provides antibodies that bind to proenkephalin and its fragments. In accordance with the invention, a kit useful for the above mentioned diagnosis is also provided.

5 Claims, 7 Drawing Sheets

Fig. 1

Proenkephalin-Sequence
(Sequence ID 1)

```
         10          20          30          40          50          60          70          80          90         100
ECSQDCATCS YRLVRPADIN FLACVMECEG KLPSLKIWET CKELLQLSKP ELPQDGTSTL RENSKPEESH LLAKRYGGFM KRYGGFMKKM DELYPMEPEE 110         120         130         140         150         160         170         180         190
EANGSEILAK RYGGFMKKDA EEDDSLANSS DLLKELLETG DNRERSHHQD GSDNEEEVSK RYGGFMRGLK RSPQLEDEAK ELQKRYGGFM
                                (P571 EEDDSLANSS DLLKE)* (TG DNRERSHHQD GSDNE PTE18)*
                                        (Sequence ID 2)              (Sequence ID 3)

200         210         220         230        240 243
RRVGRPEWWM DYQKRYGGFL KRFAEALPSD EEGESYSKEV PEMEKRYGGF MRF
(RRVGRPEWWMDYQKR PRR16)*                   (D EEGESYSKEV PEMEKR PDR18)*
        (Sequence ID 4)                             (Sequence ID 5)
```

Mature Peptides:

```
  1 –  73  Synenkephalin
 76 –  80  Met-Enk
 83 –  87  Met-Enk
 90 – 109  Propeptide 1
112 – 116  Met-Enk
119 – 159  PDS41
162 – 169  Met-Enk-Arg-Gly-Leu
172 – 183  Propeptide 2
186 – 190  Met-Enk
193 – 203  Propeptide 3
206 – 210  Leu-Enk
213 – 234  Propeptid 4
237 – 243  Met-Enk-Arg-Phe
```

*Sequences in brackets correspond to the peptides used for antibody-production

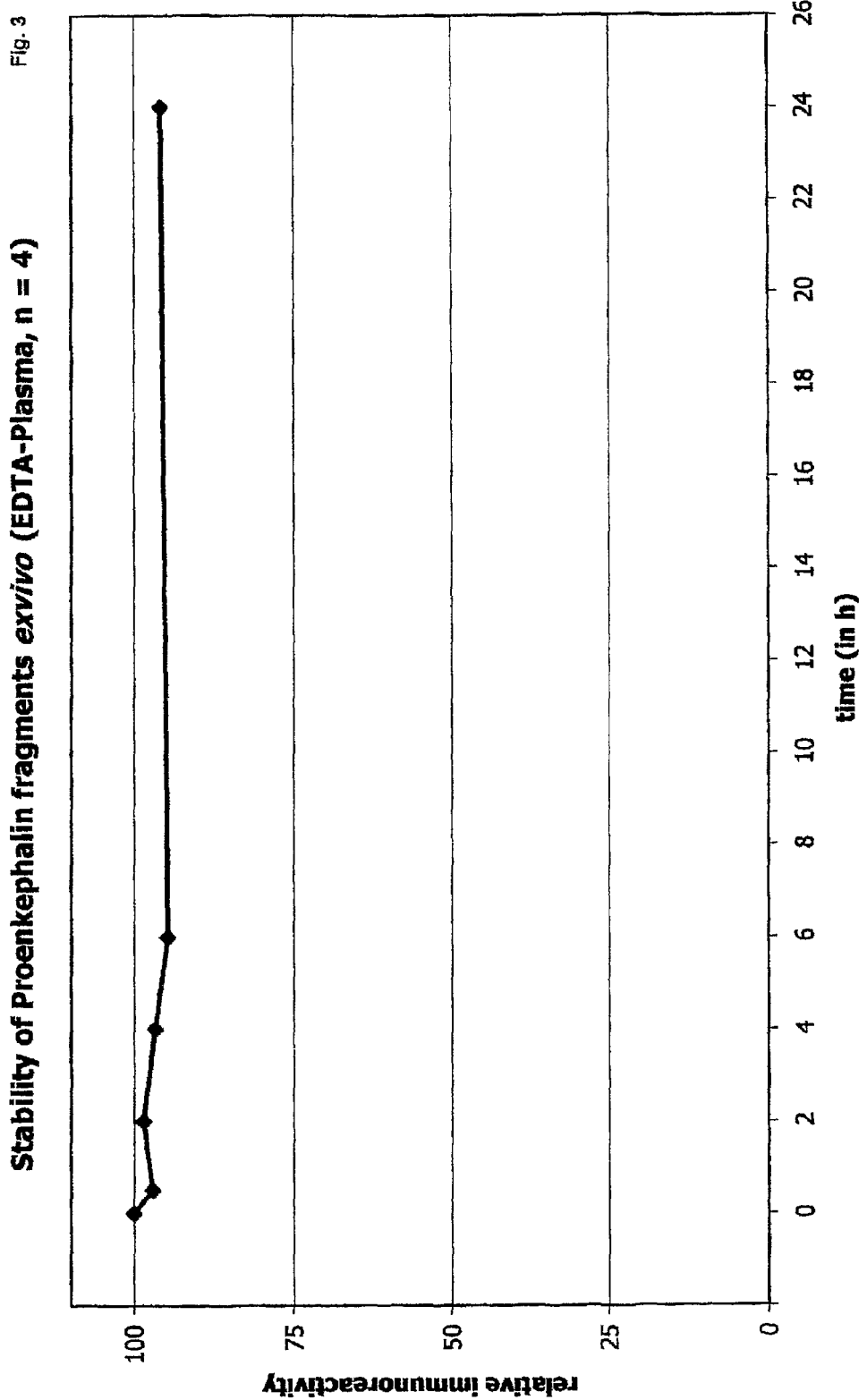

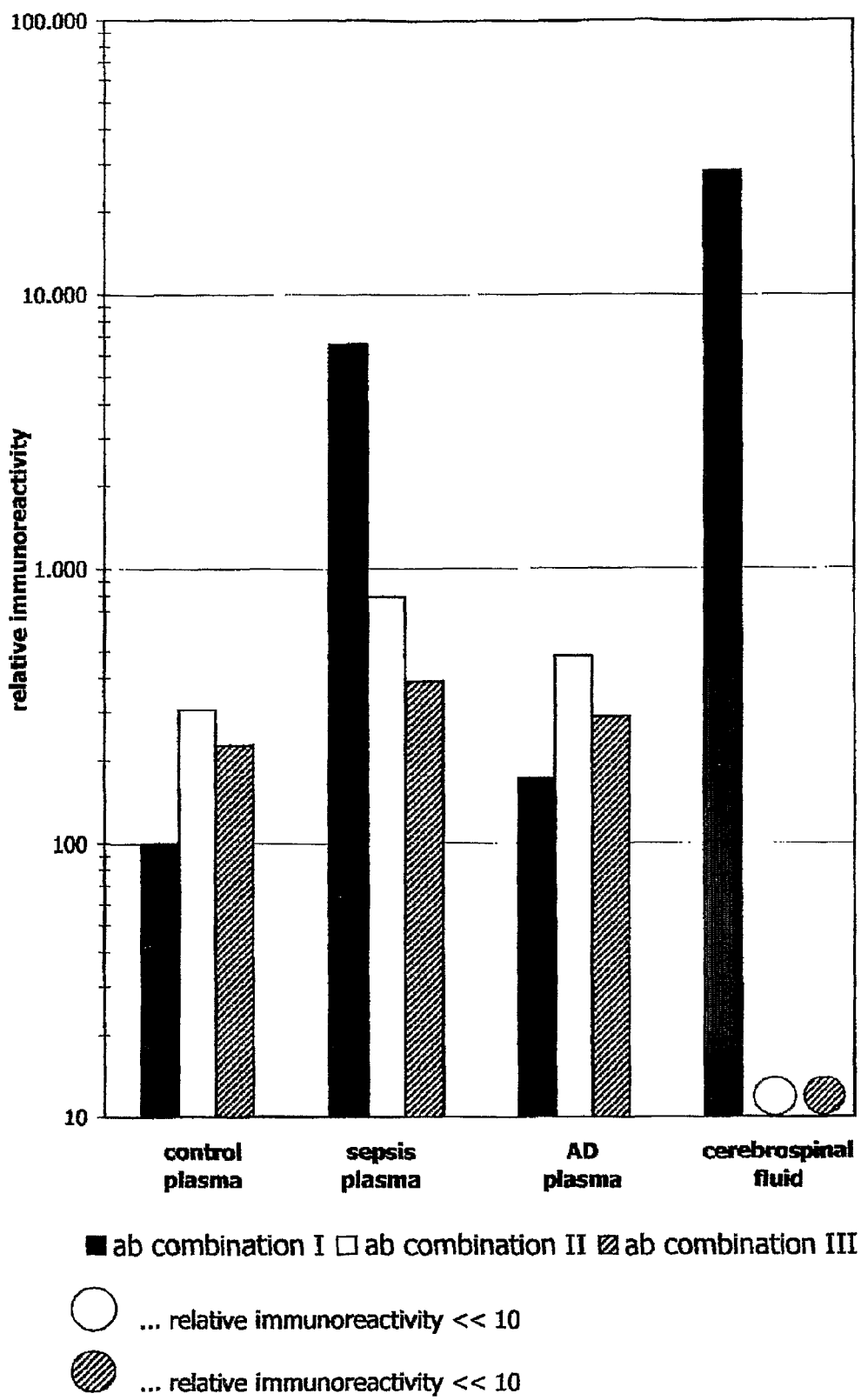

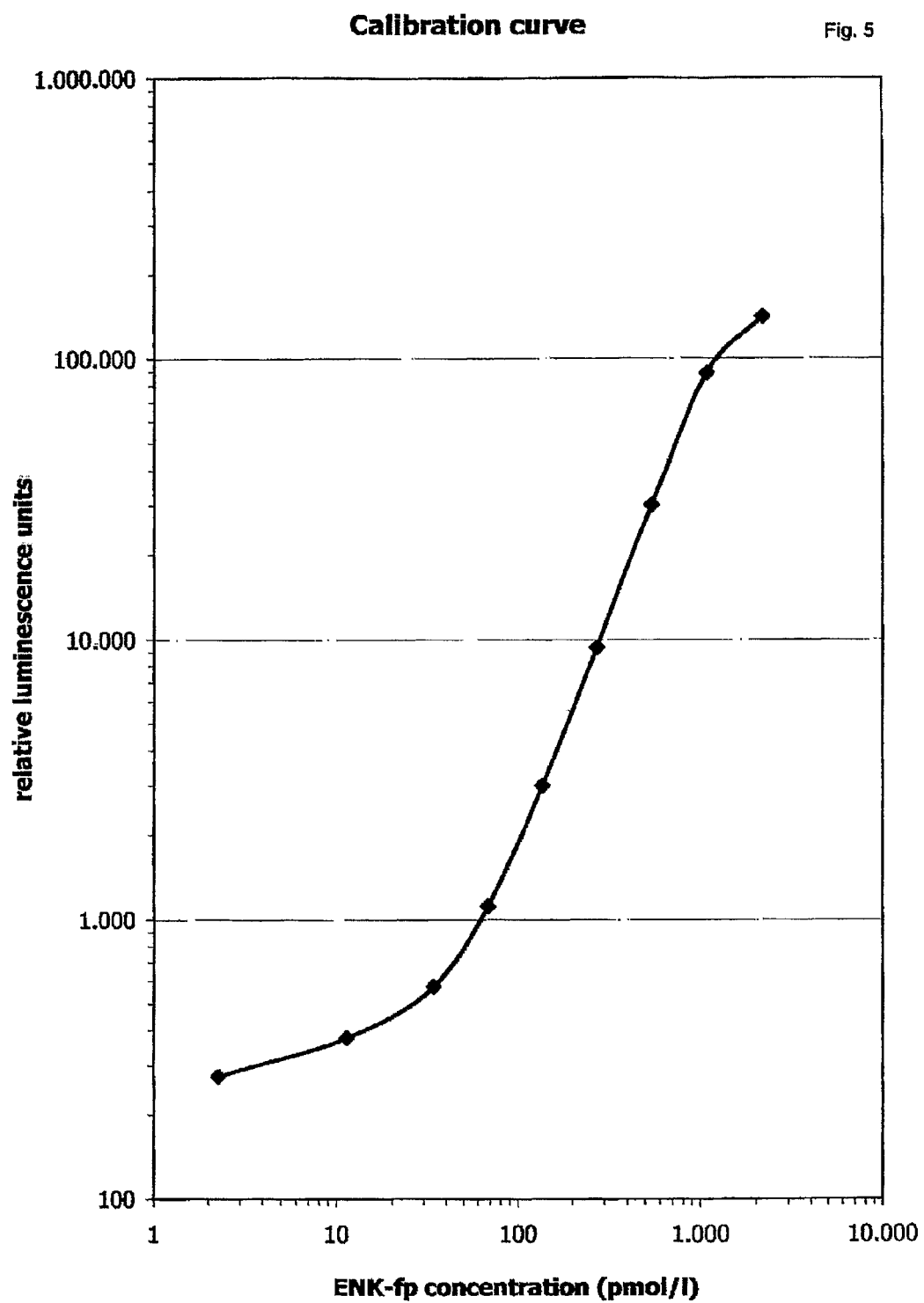

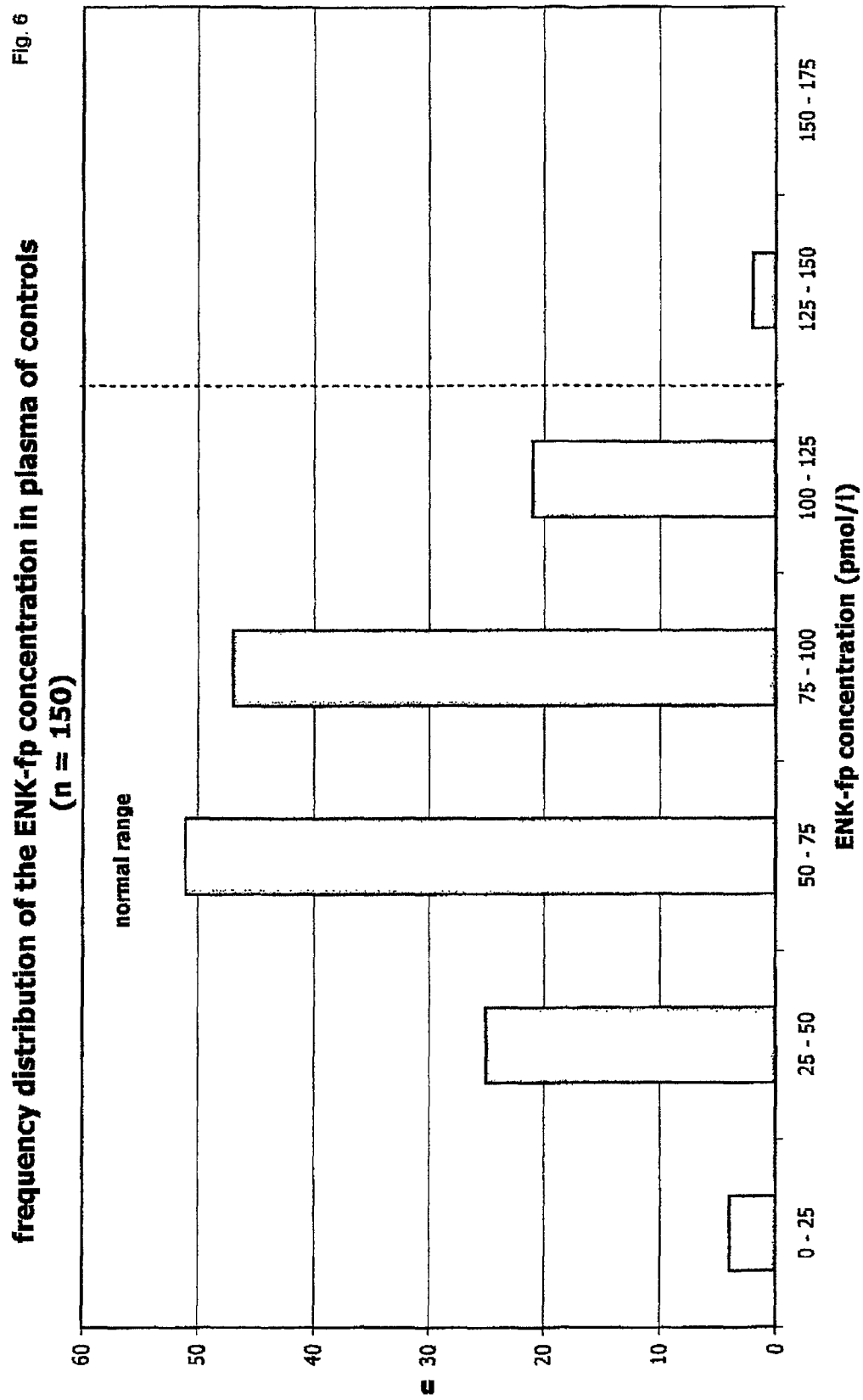

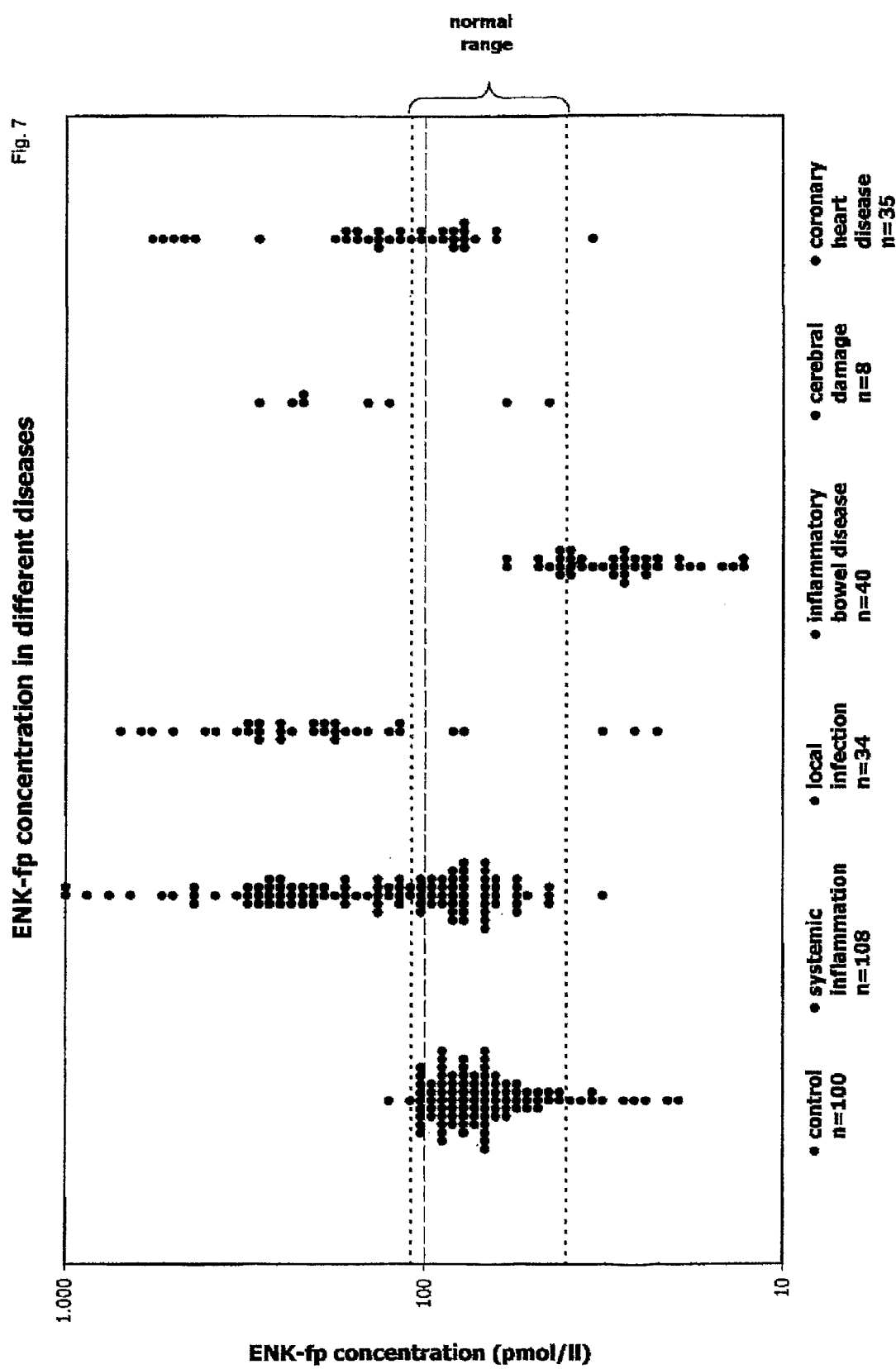

USE OF PRECURSORS OF ENKEPHALINS AND/OR THEIR FRAGMENTS IN MEDICAL DIAGNOSTICS

CROSS REFERENCE TO RELATED APPLICATIONS

This application is a 371 filing of PCT International application no. PCT/EP2005/005090 filed May 11, 2005 and published in English as WO 2005/114222 on Dec. 1, 2005 which claims the priority of European application no. 04090191.0 filed May 13, 2004. The disclosures of these applications and all other patents, published applications and other references cited herein are hereby incorporated by reference in their entirety.

The present invention relates to the use of proenkephalin and/or its fragments, fragments comprising proenkephalin and/or combinations thereof in medical diagnostics. In the following text all these molecules, fragments, combinations thereof etc. are referred to as proenkephalin comprising for example also peptide B and F, enkephalin-footprint (ENK-fp), proenkephalin A and the amino acid sequence ID 1.

Proenkephalin can be used to diagnose a variety of diseases comprising diseases/disorders of the central nervous system, neurodegenerative diseases, Parkinson's disease, Alzheimer's disease, Huntington's disease, ischemia comprising myocardiac ischemia, schizophrenia, diseases/disorders of the immune system, diseases/conditions of pain, chronic pain, migraine, tension type headache, tumor diseases/cancer comprising lymphoblastic leukaemia, malignant brain tumors, adenomas, in particular human pituitary adenomas, disorders of the blood brain barrier, multiple sclerosis, inflammation, chronic arthritis, infectious diseases, bacterial and viral infections, in particular infections of Gram-positive bacteria, borna disease virus infections, peritonitis, intoxication, AIDS, stress, trauma comprising head trauma, infarction, in particular cerebral infarction, heart and cardiovascular diseases comprising coronary heart disease, bone and skin disorders, malaria, chronic/obstructive pulmonary disease and cerebral damage.

The term proenkephalin of the present invention comprises also amino acid sequences showing at least 75% homology, preferred at least 80% homology, more preferred at least 90% homology to proenkephalin.

The invention further relates to antibodies raised against proenkephalin and/or its fragments and/or its splice variants, precursors and kits and assays involving such components.

BACKGROUND OF THE INVENTION

The human proenkephalin A gene (PENK-A) contains 4 exons and codes for a series of structurally related oligopeptides like methionine enkephalin (Met-ENK), leucine enkephalin (Leu-ENK), methionine enkephalin arginine phenylalanine (Met-ENK-Arg-Phe) as well as methionine enkephalin arginine glycin leucine (Met-ENK-Arg-Gly-Leu), wherein one molecule of proenkephalin comprises the sequences of 4 Met-ENK and one Leu-ENK, Met-ENK-Arg-Phe and Met-ENK-Arg-Gly-Leu each. Met-ENK-Arg-Phe and Met-ENK-Arg-Gly-Leu are further metabolised to Met-ENK. The enkephalins have a function as neurotransmitters as well as neuromodulators and neurohormones. PENK-A besides the enkephalins comprises the sequences of enkelytin and peptide B at its N-terminus as well as synenkephalin at its C-terminus, that have an antibacterial function.

The expression of proenkephalin occurs in the central nervous system as well as the peripheral nervous system. In the brain increased concentrations of PENK are observed in the nucleus caudatus and the nucleus accumbens, in the peri-aqueductal grey as well as in the hippocampus and the raphe nuclei.

Enkephalins play a major role in a variety of physiological processes like perception of pain, regulation of stress response comprising hormone regulation, regulation of bone formation as well as regulation of immune responses. Met-ENK stimulates the proliferation of B- and T-lymphocytes and Leu-ENK the proliferation of T-helper and cytotoxic T-cells. Due to the immune regulatory properties of Met-ENK this enkephalin is classified as cytokine. Endogenous enkephalin peptides are also involved in normal regulation of cardiovascular functions like heart frequency, contractile strength and arterial blood pressure.

Enkelytin has antibacterial function against gram-positive bacteria like *Streptococcus aureus, Bacillus megaterium* and *Micrococcus luteus*, however it is not inhibiting the growth of gram-negative bacteria like *Escherichia coli*, as well as the growth of fungi. Synenkephalin shows antibacterial properties against gram-positive bacteria as well as gram-negative bacteria.

The level of enkephalin is altered in body fluids and tissue in a variety of diseases. The Met-ENK immune reactivity in plasma of patients suffering from a brain infarctus in the acute phase and diabetes patients with symptomatic myocardiac ischemia is significantly increased as compared to healthy control individuals, as well as in plasma and liquor of patients suffering from migraine and headache and in liquor of schizophrenia patients.

In Parkinson's disease the content of Met-ENK-Arg-Gly-Leu in liquor of patients is significantly decreased as compared to healthy control individuals.

Patients suffering from Alzheimer's disease showed a 4-fold increase in Met-ENK-like immune reactivity.

The concentration of enkephalin m-RNA in the striatum of patients suffering from Huntington's disease is significantly reduced, in liquor a decrease of met-ENK-Arg-Gly-Leu concentration was shown.

In tumor diseases prolactin-(PL) and adrenocorticotropin (ACTH)-secreting adenomas of the hypophysis show an increased concentration of Met-ENK as well as a 10-fold increased concentration of proenkephalin peptides in the latter.

Enkephalins play a role in the pathophysiological response of nerve tissue in traumatic injuries like head injuries and injuries of the skin for example during and after surgery.

Enkephalins furthermore play a major role in the pathogenesis of systemic inflammations. In animal models the induction of a peritonitis or the application of lipoypolysaccarides lead to an increase in PENK-expression as well as to an increase in Met-ENK-plasma concentrations.

In abscesses of periarthritic cattle different PENK-fragments could be detected, that comprise the sequence of enkelytin. In human peripheric monocytes and rat lymphocytes the induction of PENK-m-RNA expression by lipopolysaccharides could be demonstrated:

The infection of rats by borna-viruses resulted in an increased PENK-A transcription in the striatum.

Met-ENK, Met-ENK-Arg-Phe and the proenkaphaline peptides B and F are significantly increased in plasma during hemorrhagic hypotension.

The biosynthesis of enkephalins (see FIG. 2) occurs as is the case in other peptide hormones, as preprohormone at (Golgi-) bound ribosomes. After separation of the hydrophobic N-terminal signal sequence by so-called signal peptidases and folding of the proteins in the lumen of the endoplasmic reticulum, the propeptides are packed into vesicles in the Golgi apparatus and are transported to the cell membrane. During transport the propeptides are processed to mature hormones by so-called prohormone convertases at usually dibasic amino acid sequences. Via different stimuli the peptides are secreted into the extracellular space or into the plasma. The mature peptides are rapidly inactivated after secretion by proteolysis.

Enkephalins have a half-life of 12 to 15 minutes in plasma (ex vivo).

The processing of proenkephalin occurs in several steps in a strict timely order and is tissue-specific. An earlier step in processing is the separation of the C-terminal peptide B that comprises the sequences of enkelytin and Met-ENK-Arg-Phe. The processing of proenkephalin leads to the formation of different proenkephalin peptides.

The presence of the PENK-fragment 119-159 in liquor, however not in blood, was already shown by Stark et al., 2000.

As this fragment plays a central role in this invention, it is called "enkephalin-footprint" (ENK-fp) herein.

DETAILED DESCRIPTION OF THE INVENTION

Enkephalins can be detected in different body fluids, tissues and other biomaterials.

The short half-life of enkephalins in blood ex vivo however, so far has hindered the use of enkephalins in routine diagnostics. Due to the short half-life of enkephalins, it is not possible in routine diagnostics to take samples, obtain the plasma, transport the sample into the laboratory and do the diagnostics in the laboratory including the required tests before the enkephalins reach a critical level of detection.

Thus due to the low in vivo stability of enkephalins, the use as a biomarker is extremely limited even under optimized samples logistics, as the influence of the degradation of the peptides extremely dilutes the influence of biosynthesis and enkephalin release.

The object of the invention was to overcome the disadvantageous half-life of the enkephalins and to develop a method, use and a kit for the degradation and determination of enkephalins in body fluids, tissues and other biomaterials.

This object has been achieved by the surprising finding that proenkephalin can be used as a tool for the determination of enkephalin in body fluids, tissues and other biomaterials.

This presence of the proenkephalins correlates with the presence of the mature enkephalins like Met-ENK in the different body fluids, tissues or biomaterials.

Furthermore the stability of proenkephalin, fragments and/or combinations thereof ex vivo is surprisingly high and renders the proenkephalins fully suitable for routine diagnostic purposes.

The same applies for the in vivo half-life of proenkephalin that is significantly higher than those of mature enkephalin/-s which renders them suitable to be used in the detection of enkephalin/-s concentration and release rate.

This linkage between the pro-enkephalins of the present invention and the mature peptides makes them suitable as diagnostic tools for all diseases and/or disorders, where the mature proteins like Met-ENK play a role.

Proenkephalin and fragments according to the present invention can therefore be used for diagnostics for a variety of diseases/disorders comprising diseases/disorders of the central nervous system, neurodegenerative diseases, Parkinson's disease, Alzheimer's disease, Huntington's disease, ischemia comprising myocardiac ischemia, schizophrenia, diseases/disorders of the immune system, diseases/conditions of pain, chronic pain, migraine, tension type headache, tumor diseases/cancer comprising lymphoblastic leukaemia, malignant brain tumors, adenomas, in particular human pituitary adenomas, disorders of the blood brain barrier, multiple sclerosis, inflammation, chronic arthritis, infectious diseases, bacterial and viral infections, in particular infections of Gram-positive bacteria, borna disease virus infections, peritonitis, intoxication, AIDS, stress, trauma comprising head trauma, infarction, in particular cerebral infarction, heart and cardiovascular diseases comprising coronary heart disease, bone and skin disorders, malaria, chronic/obstructive pulmonary disease and cerebral damage.

Clinical data may additionally be taken into consideration to support the determination of the disease/disorder.

The present invention in a further embodiment relates to the production of proenkephalin. It is further possible to use amino acid sequences showing at least 75% homology, preferred at least 80% homology, more preferred at least 90% homology to proenkephalin according to the present invention.

The synthesized peptides in accordance with the present invention were used to produce antigens and injected into animals to raise antibodies against the proenkephalin. Different methods can be used to achieve this object by the person skilled in the art. In a preferred embodiment hemocyanin from *Limus polyphemus* was used for the immunisation of sheep and mice. In another preferred embodiment monoclonal antibodies were produced according to methods known to a person skilled in the art. In a preferred embodiment hemocyanin from *Limus polyphemus* was used for the immunisation of mice, followed by the fusion of spleen lymphocytes of the immunized mice with a myeloma cell line to produce monoclonal antibodies.

In a preferred embodiment of the invention four amino acid sequences P571, PTE18, PRR16, PDR18 (Sequence IDs 2-5, see FIG. 1) of proenkephalin were synthesized. These sequences are comprised in the proenkephalin sequence (Sequence ID 1). The proenkephalin sequence is comprised in sequence ID 1, Sequence ID 2 comprises the peptide used for the production of antibody anti-P571, Sequence ID 3 comprises the peptide used for production of antibody anti-PTE18, Sequence ID 4 comprises the peptide used for production of antibody anti-PRR16 and Sequence ID 5 comprises the peptide used for production of antibody anti-PDR18. An amino terminal cystein residue was added to each peptide. The peptides were conjugated to a hemocyanin from *Limus polyphemus* and antibodies produced to PTE18, PRR16, PDR18 in sheep and monoclonal antibodies to P571 were produced in mice according to known methods.

Antibodies were purified according to known methods, in a preferred embodiment of the invention, this was achieved preferably by ligand specific affinity chromatography by coupling the peptides via the amino terminal cystein residue to SulfoLink-Gel of Pierce (Boston, USA) according to the methods of Pierce.

In a preferred embodiment the antibodies were tagged with a marker to enable detection. The marker used is preferably a luminescent marker and in a yet more preferred embodiment, the antibody against PTE18 was tagged with a luminescent marker.

The invention in a yet further preferred embodiment involves the use of the generated antibodies for detection of proenkephalin in body fluids, tissues or other biomaterials, as well as a kit comprising a certain quantity of such an antibody or more antibodies specific to detect proenkephalin.

Methods for the detection of binding of the antibody to the respective molecule are also known by the person skilled in the art. In one embodiment of the invention, the binding of the antibody to the target (which contains proenkephalin) is detected by luminescence.

A preferred embodiment of the invention discloses the use of antibodies generated against P571, PTE18, PRR16, PDR18. Different antibody combinations (Table 1) were used for the detection of proenkephalin in control individuals, in plasma of patients with Alzheimer's disease and of sepsis patients and liquor of healthy controls, see FIG. 4. The proenkephalin fragments detected by the antibodies are shown in Table 1.

The invention further permits the determination of the presence and stability of proenkephalin in body fluids, tissue and other biomaterials and the difference in proenkephalin concentration in healthy controls and patients of various diseases/disorders.

In one embodiment the invention is based on and uses the discovered long term stability of proenkephalin and enkephalin-fp ex vivo in plasma (FIG. 3a). In plasma proenkephalin and enkephalin-fp surprisingly have a half-life of more than 24 hours. Proenkephalin and enkephalin-fp are stable as well in liquor.

A further embodiment of the invention discloses the in vivo half-life of proenkephalin surprisingly being about 24 hours, as compared to the half-life of enkephalin.

Thus proenkephalin like enkephalin-fp is by far more suitable for diagnostic purposes than mature enkephalins which have a half-life of only 12 to 15 minutes in plasma and two minutes in vivo.

The invention further uses the correlation of proenkephalin and mature enkephalin like Met-ENK in the state of disease/disorder in body fluids, tissues or other biomaterials, blood, plasma and liquor in particular.

In one embodiment of the invention the level of immune reactivity of proenkephalin with the three antibody combinations of Table 1 of control plasma, sepsis/plasma, Alzheimer's disease/plasma and liquor of healthy controls is shown (see FIG. 4 and example 4). In the plasma of controls, sepsis and Alzheimer's patients proenkephalin could be detected using all three antibody combinations. It is shown that ENK-fp in liquor shows by far the highest concentration and shows a more than 100-fold higher signal than in the plasma of healthy controls. Also in plasma of sepsis patients the immune reactivity of ENK-fp is significantly increased. The signal is about 66-fold higher than in control plasma. Alzheimer's patients show a 1.7-fold increased signal as compared to the controls. Antibody combinations II and III do not show a detectable signal in liquor, which leads to the conclusion that proenkephalin is fully processed in liquor. In plasma however antibody combinations II and III show detectable signals, that are significantly increased in controls and Alzheimer's patients as compared to the signals of antibody combination I. Sepsis patients however show a lower signal as compared to antibody combination I.

The invention discloses the level of proenkephalin in body fluids, tissues and other biomaterials of healthy control individuals and diseased persons.

In a preferred embodiment the invention discloses the distribution of proenkephalin concentrations in plasma of healthy control individuals (FIG. 6). 95% show an immune reactivity below 109 pg/ml, the median is 74 pg/ml.

The invention further discloses a significant change of proenkephalin concentration in body fluids, tissue and other biomaterials in disease or disorder, preferentially comprising the above mentioned diseases/disorders.

A preferred embodiment of the invention is based on the surprising finding of a significant 130-fold increase of proenkephalin in liquor as compared to plasma both of healthy controls. In healthy individuals liquor contains 150 to 450 μg of protein per ml, 83% are formed in the serum and only 17% in the brain. The highest liquor-serum ratio known so far is that of prostaglandin-D-Synthetase having a value of 33. Thus the surprisingly high ratio of about 130 in the present invention is significantly higher than the ratio of all other proteins. Thus the determination of enkephalin-fp and enkephalin-fp containing immune reactivity/ratio serves as a very potent plasma marker for example for the functioning of the blood brain barrier. As the concentration of proenkephalin like proenkephalin-fp is higher in liquor than in plasma, an increase of proenkephalin in plasma indicates the damage or loss of function of the blood brain barrier: the liquor diffuses into plasma leading to an increase in proenkephalin concentration in plasma. Thus the present invention in a further embodiment provides a diagnostic method and kit for the above mentioned diseases/disorders, both having or using an antibody specific to proenkephalin, in particular enkephalin-fp.

A further preferred embodiment of the invention relates to a diagnostic method and kit for testing body samples, in particular blood, plasma or liquor with one or more antibodies specific to proenkephalin, its precursors, or fragments or combinations thereof, in particular enkephalin-fp.

A further preferred embodiment of the invention discloses a significant increase of enkephalin-fp in plasma in systemic inflammation and local infection (FIG. 7). Patients suffering from systemic inflammatory diseases surprisingly show a significantly increased value in 50% of the cases (>109 pmol/l), patients having a local infection show an increased enkephalin-fp concentration in 75% of the cases. Malaria patients had ENK-fp concentrations ranging from about 181.5 and 434 pmol/l, in a case of headache the value was about 148 pmol/l and in chronic obstructive pulmonary disease 171.5 and 251 pmol/l were measured in two patients respectively.

The invention further discloses the use of proenkephalin and/or its antibodies for detection/early detection, determination of severity, course control and prognosis of the diseases/disorders mentioned above.

DESCRIPTION OF FIGURES

FIG. 1 shows the proenkephalin sequence, the mature peptides and the sequences corresponding to the peptides used for antibody production. The proenkephalin sequence corresponds to SEQ ID NO: 1, SEQ ID NO: 2 comprises the peptide used for the production of antibody anti-P571, SEQ ID NO: 3 comprises the peptide used for production of antibody anti-PTE18, SEQ ID NO: 4 comprises the peptide used for production of antibody anti-PRR16 and SEQ ID NO: 5 comprises the peptide used for production of antibody anti-PDR18.

FIG. 3 shows the stability of proenkephalin fragments ex vivo.

FIG. 4 shows the relative immune reactivity of antibody combinations I-III in different body fluids in diseased and control individuals.

FIG. 5 shows the calibration curve of ENK-fp concentration.

FIG. 6 shows the frequency distribution of the ENK-fp concentration in plasma of controls.

FIG. 7 shows the ENK-fp concentrations in plasma of patients with systemic inflammation, local infection, inflammatory bowel disease, cerebral damage and coronary heart disease.

EXAMPLE 1

Production of Antibodies (a) Immunogen

Figure 2:
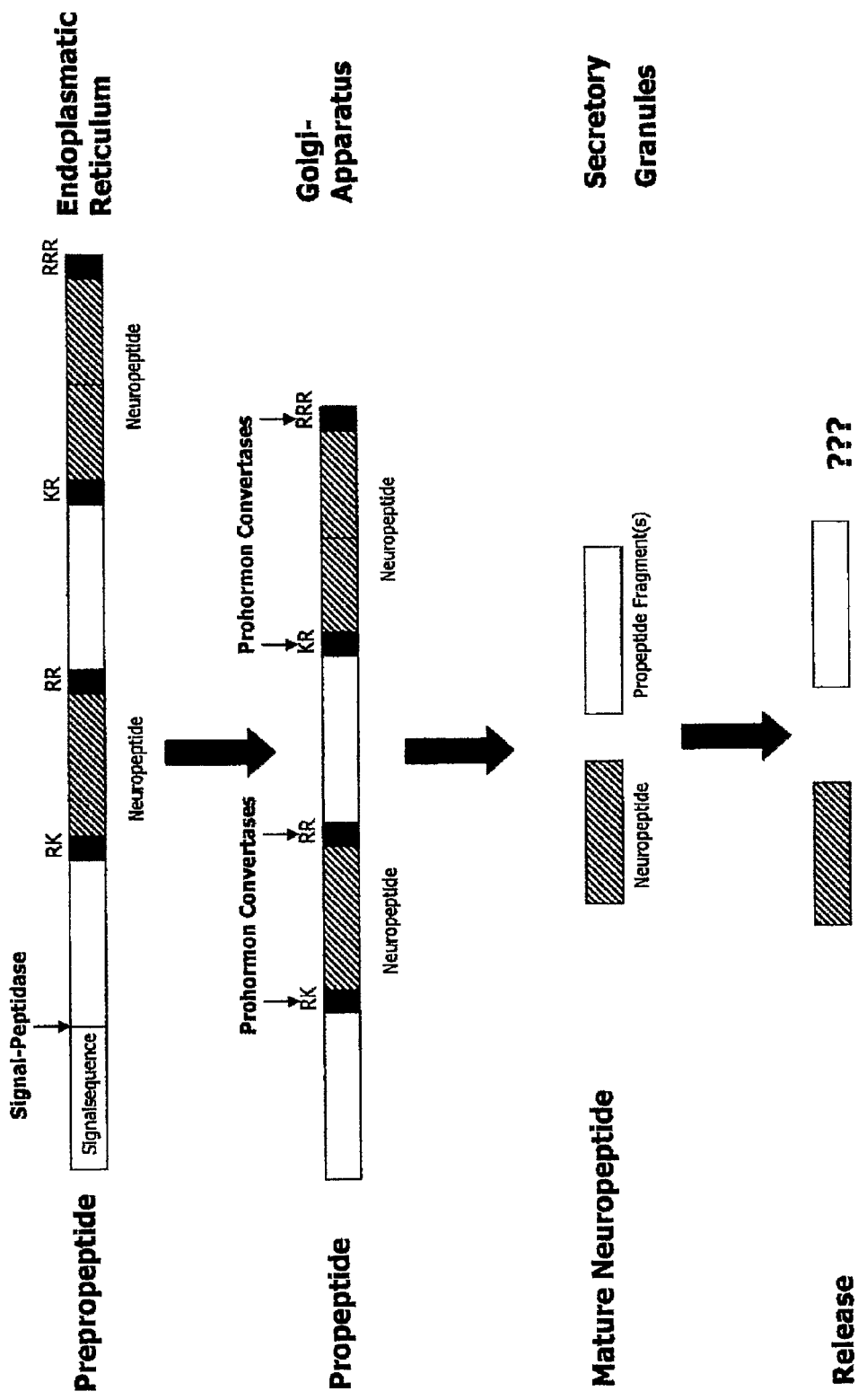
FIG. 2 shows the neuropeptide synthesis.

Four different peptide sequences (P571, PTE18, PRR16 and PDR18, see FIG. 1) of proenkephalin were selected and synthesized by Jerini (Berlin, Germany). The peptides P571 and PTE18 comprise the sequence of enkephalin-fp. PDR18 comprises 15 of 22 amino acids of the mature peptide enkelytin. Each peptide was provided with an amino terminal cystein residue (Cys0).

(b) Antibodies

For the immunization the peptides PTE18, PRR16 and PDR18 were conjugated with the hemocyanine from *Limulus polyphemus* and polyclonal antibodies were produced in sheep by Ltd. Micropharm (Carmarthenshire, Great Britain). For the production of the monoclonal antibody against the PENK-peptide P571 in mice, the peptide was conjugated with the hemocyanine of *Limulus polyphemus* by BioGenes (Berlin, Germany). Spleen lymphocytes of immunized mice were fused with a myeloma cell line and monoclonal antibodies were produced using cell cultures.

EXAMPLE 2

Purification of Antibodies

The polyclonal antibodies from sheep were purified using ligand specific affinity purification. For that step the Cys(0)-peptides PTE18, PRR16 and PDR18 were linked to SulfoLink-Gel supplied by Pierce (Boston, USA). The binding occurred according to the protocol of Pierce.

In summary, polycarbonate columns (15×80 mm) were filled with 5 ml affinity matrix. After equilibration of the columns with PBS (phosphate buffered saline: 136 mM, NaCl, 1.5 mM $KH_2PO_4$, 20.4 mM $Na_2HPO_4*2H_2O$, 2.7 mM KCl, pH 7.2) 5 mg of the respective peptide were dissolved in PBS applied to the closed columns and the gel material was homogenized by gentle rotation. After 15 minutes incubation at room temperature and settling of the gel material, the columns were washed 5 times with 3 ml PBS. To saturate free binding positions 5 ml of a 50 mM L-cysteine solution were added to the material of the column and the gel material after homogenization was again incubated for 15 minutes at room temperature. After settling of the gel material each column was washed 6 times with 5 ml of a 1 M NaCl solution followed by washing with PBS.

The gel material was mixed with 25 ml of the respective pools of antiserum and incubated over night at room temperature by gentle rotation. The serum-gel mixture was added to polycarbonate columns and surplus serum was removed. The columns were then washed with 250 ml PBS to remove unbound serum proteins. The desorption of unbound antibodies was done by elution of the column with 50 mM citric acid (pH 2.2). The eluate was captured in fractions of 1 ml. The protein concentration of each fraction was determined using the BCA-protein assay kit of Perbio (Bonn, Germany) and the fractions with a protein content >1 mg/ml were combined. The affinity purified antibodies were rebuffered in PBS via dialysis. The protein content was determined again and the antibodies were stored at 4° C.

Monoclonal Antibodies:

The monoclonal antibody against the PENK-peptide P571 was purified via protein G affinity chromatography from cell supernatant. An Eco-plus-Column (10 mm×125 mm) of Kronlab (Sinsheim, Germany) was loaded with 25 ml affinity chromatography medium Prosep-G of Millipore (Schwalbach, Germany).

EXAMPLE 3

Immobilization/Tagging of the Antibodies

The purified antibodies against the peptides P571, PRR16 and PDR18 were immobilized on polystyrol tubes (Startubes, 12 m×75 mm, Greiner, Germany). For that procedure the antibody solutions were diluted to a protein concentration of 6.7 µg/ml with PBS and 300 µl per tube were pipetted (corresponds to 2 µg antibody per tube). These were incubated for 20 hours at room temperature and then washed 3 times with 4 ml PBS, respectively. Until further use the tubes were stored at 4° C.

The antibody against PTE18 (1 mg/ml in PBS) was tagged with the luminescent marker acridiniumester-N-hydroxysuccinimid (1 mg/ml in acetonitrile, InVent, Hennigsdorf, Germany). For the tagging procedure 200 µl of antibody were mixed with 4 µl acridinium ester, incubated for 20 minutes and free acridinium ester bonds were saturated by adding 40 µl of a 50 mM glycine solution. The tagging preparation was separated from free acridinium ester by HPLC in a BioSil 400-gel filtration column (BioRad, Munich, Germany). PBS was used a solvent.

EXAMPLE 4

Determination of the Proenkephalin Immune Reactivity

The proenkephalin immune reactivity was determined in plasma using three different combinations of antibodies of 5 controls each, sepsis and Alzheimer's patients as well as in the liquor of 5 control individuals.

100 µl of sample were pipetted in each tube coated with antibody and 20 ng of the tagged antibody (in 200 µl PBS buffer, 10 mM EDTA) were added. The tubes were incubated for 20 hours at 4° C. and subsequently tracer antibody was removed by washing 5 times with 1 ml PBS. Tagged antibody bound to the tube was quantified by measuring the luminescence in a luminometer (Berthold LB 952T/16).

The measured relative immune reactivities of the different antibody combinations are shown in FIG. 4.

In the plasma of controls, sepsis and Alzheimer's patients proenkephalin sequences could be detected using all three antibody combinations. The average value of the control data of antibody combination I was calibrated to 100% for a better comparison of the results and the average values of the remaining data were referred to that (see Table 1). It is shown that enkephalin-fp in liquor shows by far the highest concentration and shows a 280-fold higher signal than the plasma of healthy controls. Also in plasma of sepsis patients the immune reactivity of enkephalin-fp is significantly increased. The signal is about 66-fold higher than in control plasma. Alzheimer's patients show a 1.7-fold increased signal as compared to the controls. Antibody combinations II ad III do not show a detectable signal in liquor, which leads to the conclusion that proenkephalin is fully processed in liquor. In plasma however antibody combinations II and III showed detectable signals, that were are significantly increased in controls and Alzheimer's patients as compared to the signals of antibody combination I. Sepsis patients however show a lower signal as compared to antibody combination I. Thus this combination is a better method for the differentiation of sepsis patients and controls.

TABLE 1

Measurement of the relative immune reactivity of proenkephalin in combination with different antibody combinations

| | Antibody combination | | | | | |
|---|---|---|---|---|---|---|
| | I (P571/ PTE18) | | II (PRR16/ PTE18) | | III (PRR16/ PTE18) | |
| Sample | rel. IR | ratio | Rel. IR | ratio | Rel. IR | ratio |
| Control plasma | 100 | 1.0 | 305 | 1 | 227 | 1 |
| Sepsis plasma | 6.622 | 66.2 | 792 | 2.6 | 388.5 | 1.7 |
| Alzheimer plasma | 172 | 1.7 | 482 | 1.6 | 289 | 1.3 |
| CSF | 28.278 | 282.8 | 8.5 | 0.028 | 4.5 | 0.0199 |

Rel. IR: relative immune reactivity (values in % in response to the control plasma value of antibody combination I which was calibrated to 100%). All values are average values (n = 5). Ratio: ratio of the respective value of the patient (in %) and the corresponding control value (in %) of the respective antibody combination.

EXAMPLE 5

Immunoassay for the Quantitative Determination of Enkephalin-fp

Components:

Tubes coated with P571-antibodies and the antibody against PTE-18 tagged with a luminescent marker were used in the immunoassay. The production of these components is described in example 3.

Procedure:

100 µl of sample were pipetted in each tube coated with antibody and 20 ng of the tagged antibody (in 100 µl PBS-buffer, 10 mM EDTA) were added. The tubes were incubated for 20 hours at 4° C. followed by removal of tracer antibody by washing 5 times with 1 ml PBS. Tagged antibodies bound to the tube was quantified by measuring the luminescence in a luminometer (Berthold LB 952T/16).

Calibration

To be able to determine the concentrations and the immune reactivities of enkephalin-fp, the peptide was synthesized by Jerini (Berlin, Germany). The weighed out peptide was used as a calibrator for the immune assay. In FIG. 5 the standard curve of enkephalin-fp is shown. The analytical sensitivity of the enkephalin-fp assay is about 11 pmol/l.

EXAMPLE 6

ENK-fp Concentration in Plasma of Supposedly Healthy Individuals (Controls)

The distribution curve of the ENK-fp concentration in plasma of healthy individuals is shown in FIG. 6. 95% of the 150 healthy individuals show an ENK-fp concentration in a tight array between 40 and 100 pmol/.

EXAMPLE 7

ENK-fp Concentration in Cerebrospinal Fluid (CSF)

The ENK-fp concentration in liquor of control samples (n=39) was determined and a median of 9623 pmol/l was determined. The CSF-median is increased significantly by a factor of about 130 above the median of plasma of healthy control individuals. In healthy individuals liquor contains 150 to 450 µg of protein per ml, 83% are formed in the serum and only 17% in the brain. The highest liquor-serum ratio known so far is that of prostaglandin-D-Synthetase having a value of 33. Thus the surprisingly high ratio of about 130 in the present invention is significantly higher than the ratio of all other proteins. Thus the determination of enkephalin-fp and enkephalin-fp containing immune reactivity/ratio serves as a very potent plasma marker for the functioning of the blood brain barrier.

EXAMPLE 8

Determination of ENK-fp Concentration in the Blood Circulation of Patients Suffering from Systemic Inflammations Local Infections and Other Diseases Patients suffering from systemic inflammatory diseases showed significantly increased values in 50% of the cases (>109 pmol/l, see FIG. 7). Also patients having a local infection (e.g. abscesses) showed an increased ENK-fp concentration in 75% of the cases (see FIG. 7).

Furthermore increased concentrations of ENK-fp were determined in Alzheimer's disease, cerebral damage and coronary heart disease in 75 and 54% respectively (FIG. 7). A significant decrease of enkephalin-fp concentration could be detected in 75% of patients having inflammatory bowel disease like Crohn's disease or colitis ulcerosa.

Malaria patients had ENK-fp concentrations ranging from about 181.5 and 434 pmol/l, in a case of headache the value was about 148 pmol/l and in chronic obstructive pulmonary disease 171.5 and 251 pmol/l were measured in two patients respectively.

LITERATURE

Starck, M., Danielsson, O., Griffith, A. J., Jörnvall, H., Johannsson, J. (2001): "Peptide repertoire of human cerebrospinal fluid: novel proteolytic fragments of neuroendocrine proteins". Journal of Chromatography Vol. 754, p. 357-367.

The invention claimed is:

1. An isolated antibody that specifically binds a peptide consisting of the amino acid sequence of SEQ ID NO: 2.

2. The isolated antibody of claim 1, wherein said antibody is generated by immunization with a peptide consisting of the amino acid sequence of SEQ ID NO.: 2.

3. An isolated antibody that specifically binds a peptide consisting of the amino acid sequence of SEQ ID NO: 3.

4. A kit for an immunological assay comprising:
   at least one antibody that specifically binds to a peptide consisting of the amino acid sequence of SEQ ID NO: 2; and
   at least one antibody that specifically binds to a peptide consisting of the amino acid sequence of SEQ ID NO: 3.

5. The kit of claim 4, wherein said first antibodies are generated by immunization of an animal with a peptide consisting of the amino acid sequence of SEQ ID NO.: 2.

* * * * *

UNITED STATES PATENT AND TRADEMARK OFFICE
CERTIFICATE OF CORRECTION

| | | |
|---|---|---|
| PATENT NO. | : 8,013,123 B2 | Page 1 of 1 |
| APPLICATION NO. | : 11/569023 | |
| DATED | : September 6, 2011 | |
| INVENTOR(S) | : Bergmann et al. | |

It is certified that error appears in the above-identified patent and that said Letters Patent is hereby corrected as shown below:

On the title page;

In the Assignee (73): Delete "B.R.A.H.M.S. GmbH" and insert -- B.R.A.H.M.S GmbH --

Signed and Sealed this

Twenty-fifth Day of October, 2011

David J. Kappos
*Director of the United States Patent and Trademark Office*

SEQUENCE LISTING

<160> NUMBER OF SEQ ID NOS: 5

<210> SEQ ID NO 1
<211> LENGTH: 243
<212> TYPE: PRT
<213> ORGANISM: Artificial
<220> FEATURE:
<223> OTHER INFORMATION: Synthetic -continued

<400> SEQUENCE: 1

Glu Cys Ser Gln Asp Cys Ala Thr Cys Ser Tyr Arg Leu Val Arg Phe
1               5                   10                  15

Ala Asp Ile Asn Phe Leu Ala Cys Val Met Glu Cys Glu Gly Lys Leu
            20                  25                  30

Pro Ser Leu Lys Ile Trp Glu Thr Cys Lys Glu Leu Leu Gln Leu Ser
        35                  40                  45

Lys Pro Glu Leu Pro Gln Asp Gly Thr Ser Thr Leu Arg Glu Asn Ser
    50                  55                  60

Lys Pro Glu Glu Ser His Leu Leu Ala Lys Arg Tyr Gly Gly Phe Met
65                  70                  75                  80

Lys Arg Tyr Gly Gly Phe Met Lys Lys Met Asp Glu Leu Tyr Pro Met
                85                  90                  95

Glu Pro Glu Glu Glu Ala Asn Gly Ser Glu Ile Leu Ala Lys Arg Tyr
            100                 105                 110

Gly Gly Phe Met Lys Lys Asn Ala Glu Glu Asp Ser Leu Ala Asn
            115                 120                 125

Ser Ser Asp Leu Leu Lys Glu Leu Leu Glu Thr Gly Asp Asn Arg Glu
130                 135                 140

Arg Ser His His Gln Asp Gly Ser Asp Asn Glu Glu Val Ser Lys
145                 150                 155                 160

Arg Tyr Gly Gly Phe Met Arg Gly Leu Lys Arg Ser Pro Gln Leu Glu
                165                 170                 175

Asp Glu Ala Lys Glu Leu Gln Lys Arg Tyr Gly Gly Phe Met Arg Arg
            180                 185                 190

Val Gly Arg Pro Glu Trp Trp Met Asp Tyr Gln Lys Arg Tyr Gly Gly
                195                 200                 205

Phe Leu Lys Arg Phe Ala Glu Ala Leu Pro Ser Asp Glu Glu Gly Glu
210                 215                 220

Ser Tyr Ser Lys Glu Val Pro Glu Met Glu Lys Arg Tyr Gly Gly Phe
225                 230                 235                 240

Met Arg Phe

<210> SEQ ID NO 2
<211> LENGTH: 14
<212> TYPE: PRT
<213> ORGANISM: Artificial
<220> FEATURE:
<223> OTHER INFORMATION: Synthetic

<400> SEQUENCE: 2

Glu Glu Asp Asp Ser Leu Ala Asn Ser Ser Asp Leu Leu Lys
1               5                   10

<210> SEQ ID NO 3
<211> LENGTH: 16
<212> TYPE: PRT
<213> ORGANISM: Artificial
<220> FEATURE:
<223> OTHER INFORMATION: Synthetic

<400> SEQUENCE: 3

Thr Gly Asp Asn Arg Glu Arg Ser His His Gln Asp Gly Ser Asp Asn
1               5                   10                  15

<210> SEQ ID NO 4
<211> LENGTH: 15
<212> TYPE: PRT
<213> ORGANISM: Artificial

-continued

```
<220> FEATURE:
<223> OTHER INFORMATION: Synthetic

<400> SEQUENCE: 4

Arg Arg Val Gly Arg Pro Glu Trp Trp Met Asp Tyr Gln Lys Arg
1               5                   10                  15

<210> SEQ ID NO 5
<211> LENGTH: 16
<212> TYPE: PRT
<213> ORGANISM: Artificial
<220> FEATURE:
<223> OTHER INFORMATION: Synthetic

<400> SEQUENCE: 5

Asp Glu Glu Gly Glu Ser Tyr Ser Lys Glu Val Pro Glu Met Glu Lys
1               5                   10                  15
```